(12) United States Patent
Zadno

(10) Patent No.: US 7,556,632 B2
(45) Date of Patent: Jul. 7, 2009

(54) DEVICE AND METHOD FOR REPAIRING TISSUE

(76) Inventor: Reza Zadno, 47066 Palo Amarillo Dr., Fremont, CA (US) 94539

( * ) Notice: Subject to any disclaimer, the term of this patent is extended or adjusted under 35 U.S.C. 154(b) by 0 days.

(21) Appl. No.: 11/249,910

(22) Filed: Oct. 12, 2005

(65) Prior Publication Data

US 2006/0030867 A1 Feb. 9, 2006

Related U.S. Application Data

(63) Continuation-in-part of application No. 11/178,220, filed on Jul. 8, 2005, now abandoned.

(60) Provisional application No. 60/586,816, filed on Jul. 9, 2004.

(51) Int. Cl.
*A61B 17/10* (2006.01)

(52) U.S. Cl. ............................ 606/142; 606/213

(58) Field of Classification Search ............. 606/139, 606/142, 151, 213, 215, 143
See application file for complete search history.

(56) References Cited

U.S. PATENT DOCUMENTS

| 6,629,534 | B1 | 10/2003 | St. Goar et al. | 128/898 |
|---|---|---|---|---|
| 6,641,593 | B1 * | 11/2003 | Schaller et al. | 606/157 |
| 6,749,621 | B2 * | 6/2004 | Pantages et al. | 606/213 |
| 6,752,813 | B2 * | 6/2004 | Goldfarb et al. | 606/139 |
| 6,818,009 | B2 * | 11/2004 | Hart et al. | 606/232 |
| 7,112,207 | B2 * | 9/2006 | Allen et al. | 606/139 |
| 7,320,692 | B1 * | 1/2008 | Bender et al. | 606/139 |

FOREIGN PATENT DOCUMENTS

| WO | WO99/00059 | 1/1999 |
|---|---|---|
| WO | WO00/60995 | 10/2000 |

OTHER PUBLICATIONS

C. Fucci et al. "Improved Results With Mitral Valve Repair Using New Surgical Techniques" (1995) Eur. J. Cardio-Thorac Surg. 9: 621-627.

* cited by examiner

*Primary Examiner*—Todd E Manahan
*Assistant Examiner*—Lindsey Bachman
(74) *Attorney, Agent, or Firm*—Lumen Patent Firm

(57) ABSTRACT

A tissue-stapling device for repairing tissue is provided. The device has two guiding elements movable with respect to each other. Self-deployable wings are located on the outside of the inner guiding element, which are used for stabilizing tissue parts with respect to the device. A self-deployable clip with two or more edges can be advanced through the inner guiding element and is capable of penetrating the tissue parts. The self-deployable clip is sized so that it can be positioned against the tissue parts. The device further includes a clip penetrating mechanism that is capable of moving through the inner guiding element and is capable of penetrating the clip through the tissue parts and therewith securing the tissue parts clipped or stapled together.

7 Claims, 12 Drawing Sheets

DEVICE AND METHOD FOR REPAIRING TISSUE

CROSS-REFERENCE TO RELATED APPLICATIONS

This application is a Continuation-In-Part (CIP) of U.S. Non-Provisional patent application Ser. No. 11/178,220 filed on Jul. 8, 2005 now abandoned. This application claims the benefit of U.S. Non-Provisional patent application Ser. No. 11/178,220 filed on Jul. 8, 2005, now abandoned, which claims the benefit of U.S. Provisional Application 60/586,816 filed on Jul. 9, 2004, which are both hereby incorporated by reference.

FIELD OF THE INVENTION

The present invention relates generally to surgical procedures and techniques. More particularly, it relates to methodologies and devices useful in repairing cardiac valves such as the mitral valve. This invention can also be used in other applications where percutaneous placement of clips or attachments is necessary, for example, interventions to treat obesity, urinary incontinence, hernia, and anastomosis.

BACKGROUND

Surgically suturing the flaps of the mitral valve eliminates regurgitation. As discussed by C. Fucci et al. in European Journal of Cardio-Thoracic Surgery Springer-Verlag 1995, good results are obtained using PTFE sutures for joining the prolapsing free edge of one leaflet to the facing edge of the posterior leaflet. This is also discussed in the U.S. Pat. No. 6,629,534, issued to Evalve, Inc., which describes an intricate endovascular surgical technique that enables a minimally invasive way of repairing the mitral valve. More specifically, the Evalve patent teaches an interventional tool that is advanced to the ventricle to be engaged against and modifies the valve leaflets in a manner that reduces leakage through the valve during ventricular systole. As one skilled in the art will appreciate, there is a continuing need in the field of medicine for better endovascular surgical techniques and devices that are more efficient, less invasive, and more effective.

SUMMARY OF THE INVENTION

The present invention provides a tissue-stapling device for repairing tissue. The device has two guiding elements, i.e., a first guiding element with a first opening and a second guiding element with a second opening. The second guiding element is sized to be movable through the first opening of the first guiding element.

Two or more self-deployable wings are located on the outside of the second guiding element. The wings have an un-deployed state to move through the first guiding element, and a deployed state for when they are advanced passed the first opening of the first guiding element. In self-deployed state the wings are capable of stabilizing two or more tissue parts with respect to the device.

The device further includes a self-deployable clip with two or more edges capable of penetrating the tissue parts. The self-deployable clip has a un-deployed state for advancing through the second opening and a deployed state for when advanced passed the second opening. The self-deployable clip is sized so that it can be positioned against the tissue parts.

The device further includes a clip penetrating mechanism that is capable of moving through the second opening. The clip penetrating mechanism has a top part with a first state for advancing through the second opening and a second state whereby the top part is bend, unfolded or uncompressed and capable of penetrating the clip through the tissue parts, e.g. by retracting the clip penetrating mechanism and/or action of the top part in its second state.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Figure 1:
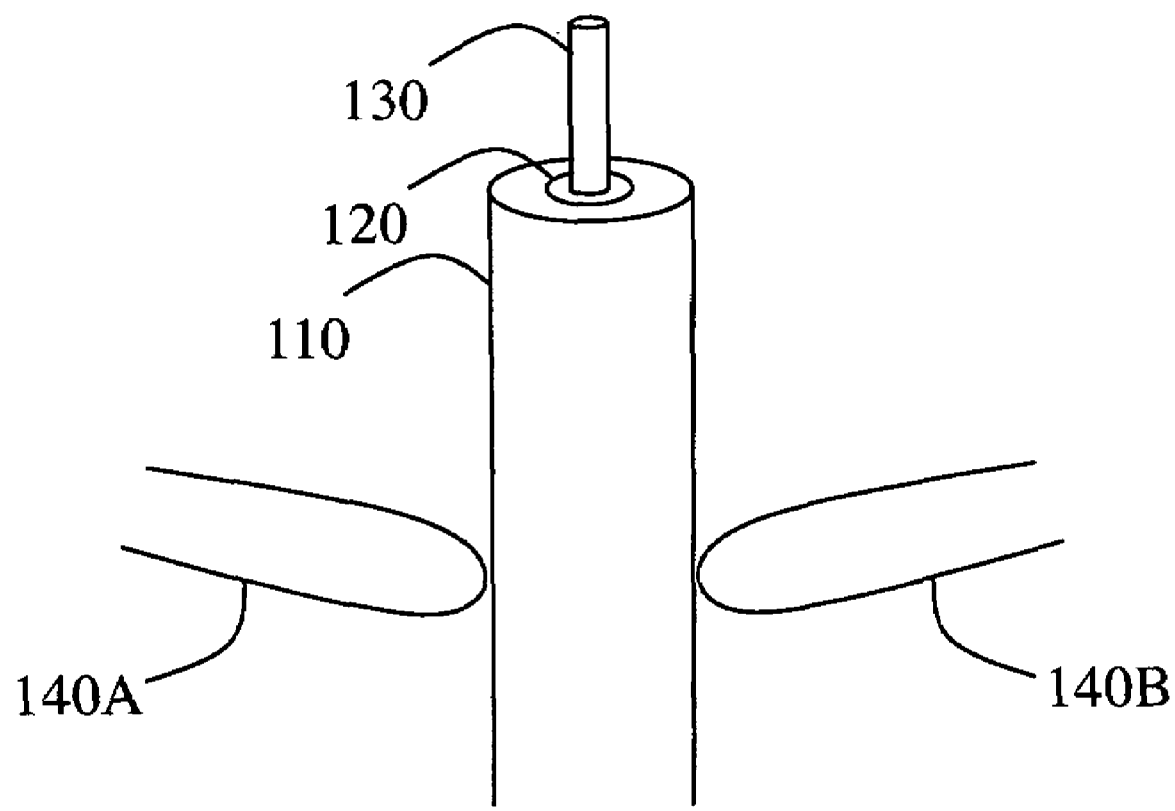
FIG. 1 shows a first guiding element 110, a second guiding element 120, a guide wire 130 and two tissue parts 140A, 140B (e.g. flaps of a left atrium).
Figure 2:
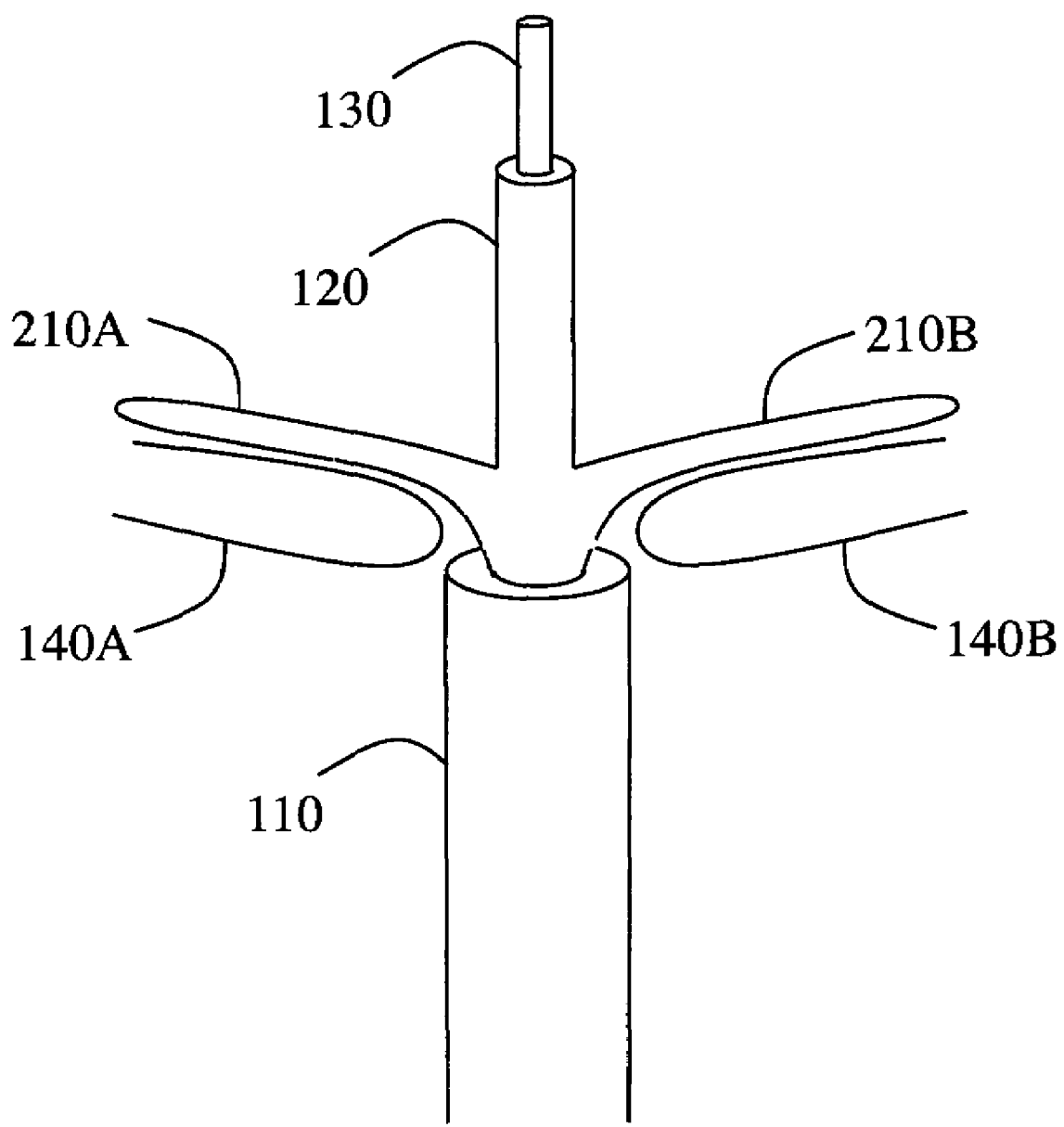
FIG. 2 shows two wings 210A, 210B (also referred to as flap support) that changed from an un-deployed state (when inside first guiding element 110) to a deployed state when guiding element 120 is advanced through the opening of the first guiding element 110.
Figure 3:
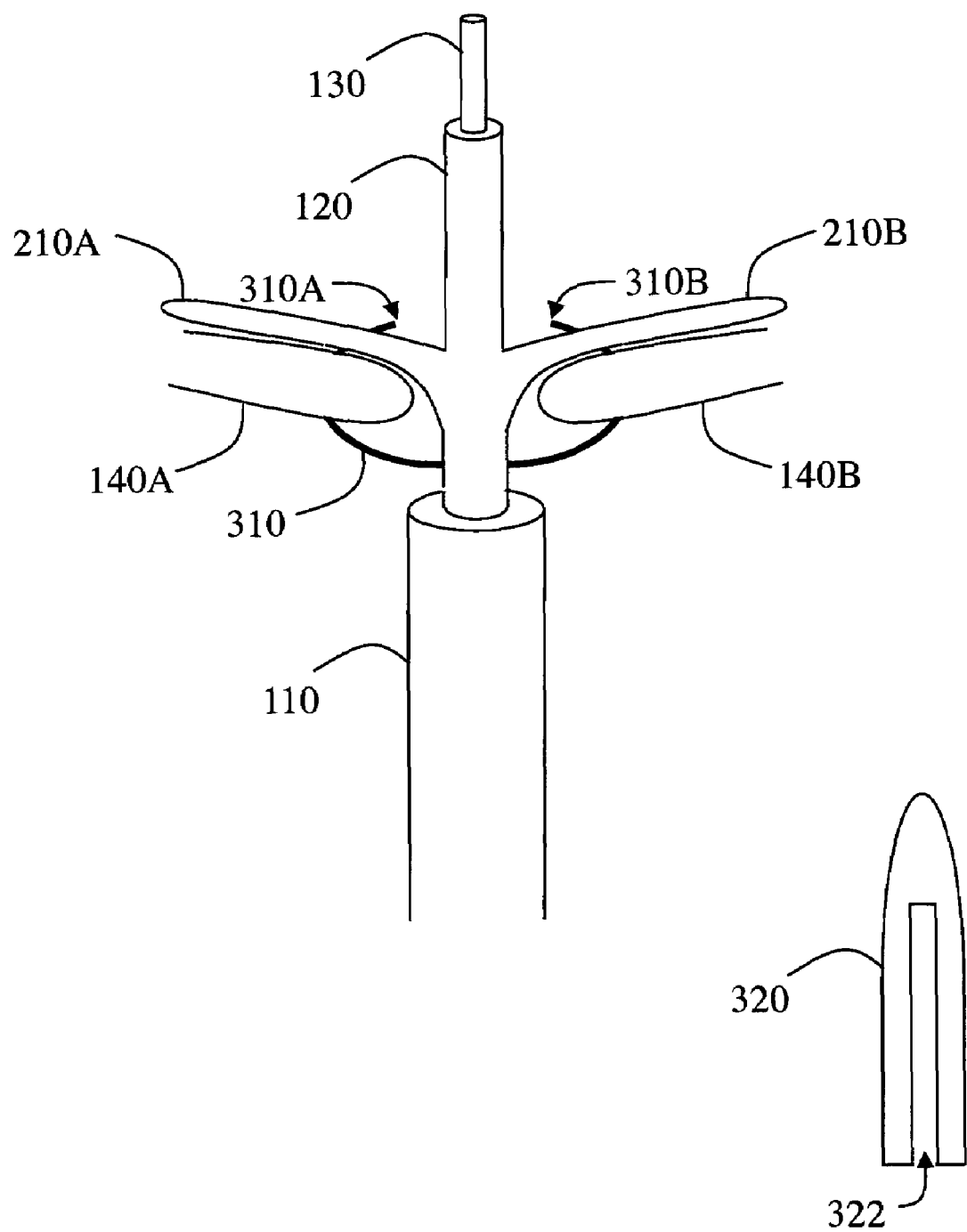
FIG. 3 shows a deployable clip 310 having two or more (sharp) edges 310A, 310B. Deployable clip 310 is shown in a deployed state and penetrated through tissue parts 140A, 140B. Deployable clip 310 is in un-deployed state when second guiding element 120 is retracted in first guiding element 110. Wings 210A, 210B have an opening for deployable clip 310 as shown by a top view of wing 320 with opening 322.
Figure 4:
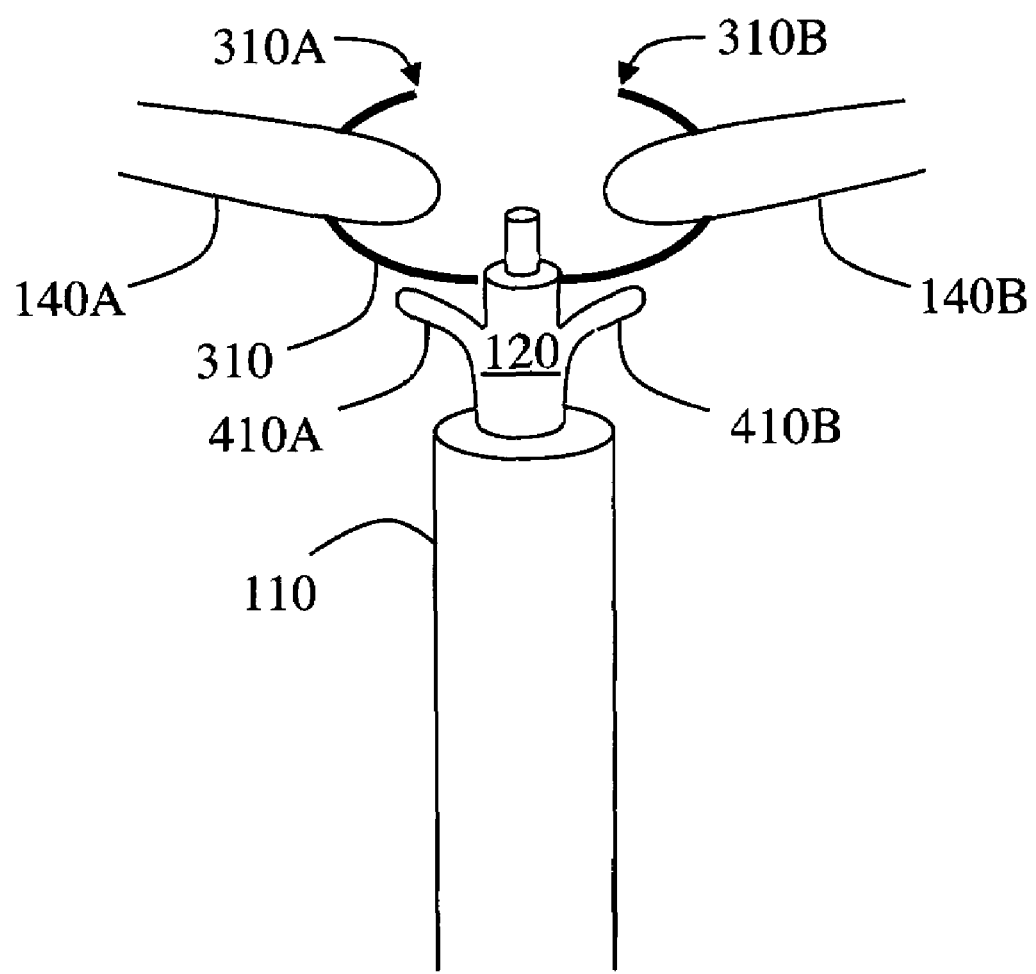
FIG. 4 shows second guiding element 120 with wings 410A, 410B retracted leaving deployable clip 310 through tissue parts 140A, 140B.
Figure 5:
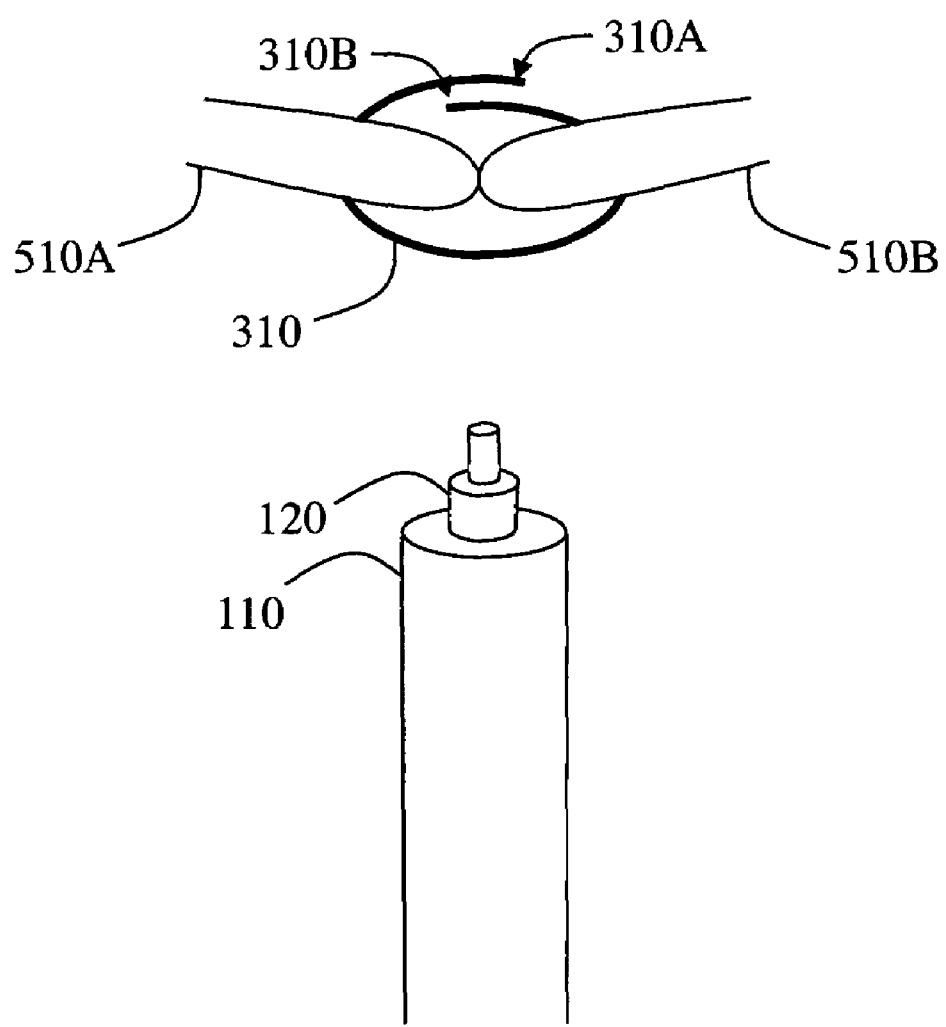
FIG. 5 shows deployable clip 310 through tissue parts 140A, 140B placing tissue parts 140A, 140B in a repaired position 510A, 510B.
Figure 6:
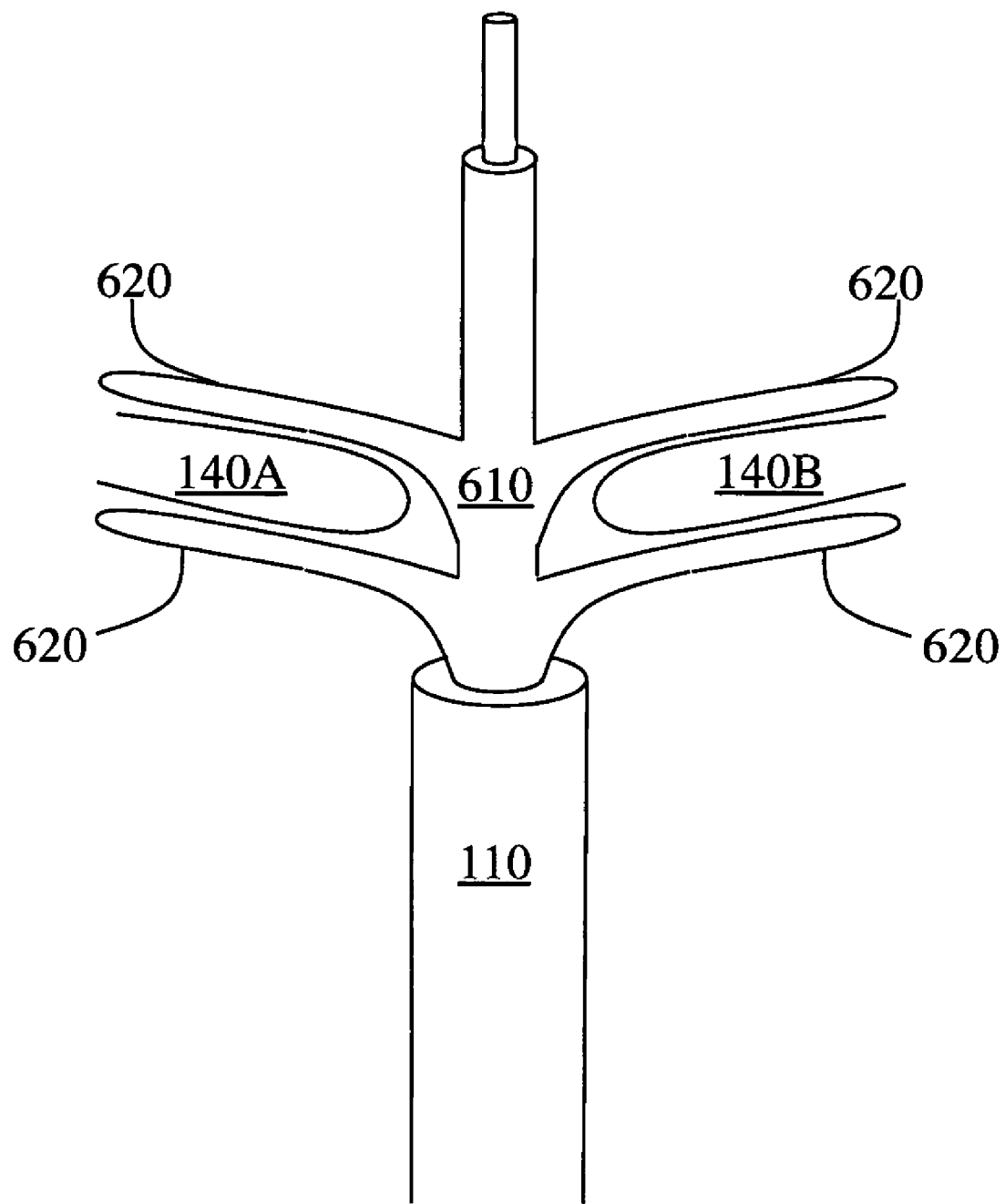
FIG. 6 shows a variation of a second guiding element 610 with two sets of deployable wings 620.
Figure 7:
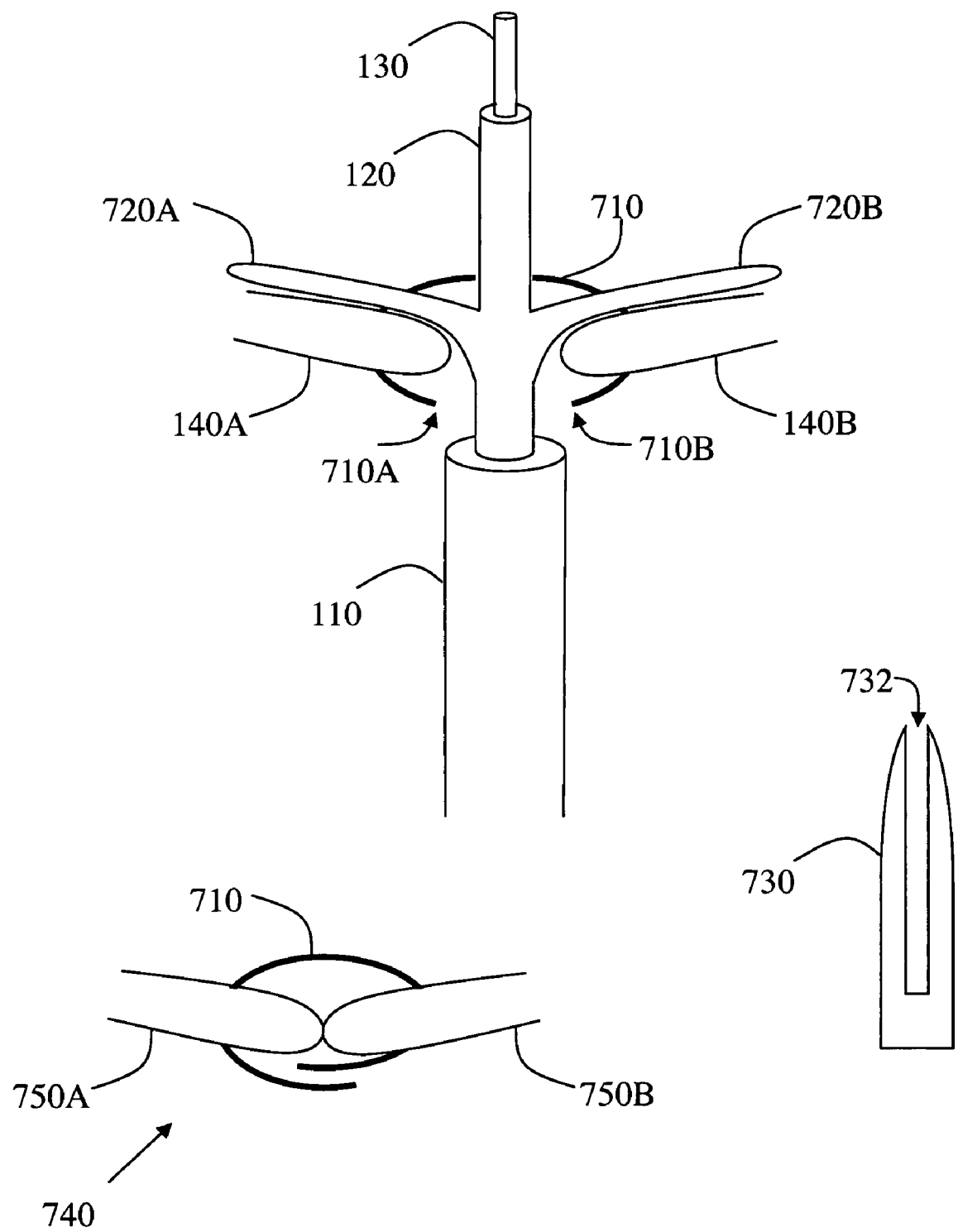
FIG. 7 shows a variation with a deployable clip 710 having two or more (sharp) edges 710A, 710B that can be deployed from above wings 720A, 720B. Wings 720A, 720B have an opening for deployable clip 710 as shown by a top view of wing 730 with opening 732. 740 shows deployable clip 710 through tissue parts 140A, 140B placing tissue parts 140A, 140B in a repaired position 750A, 750B.
Figure 8:
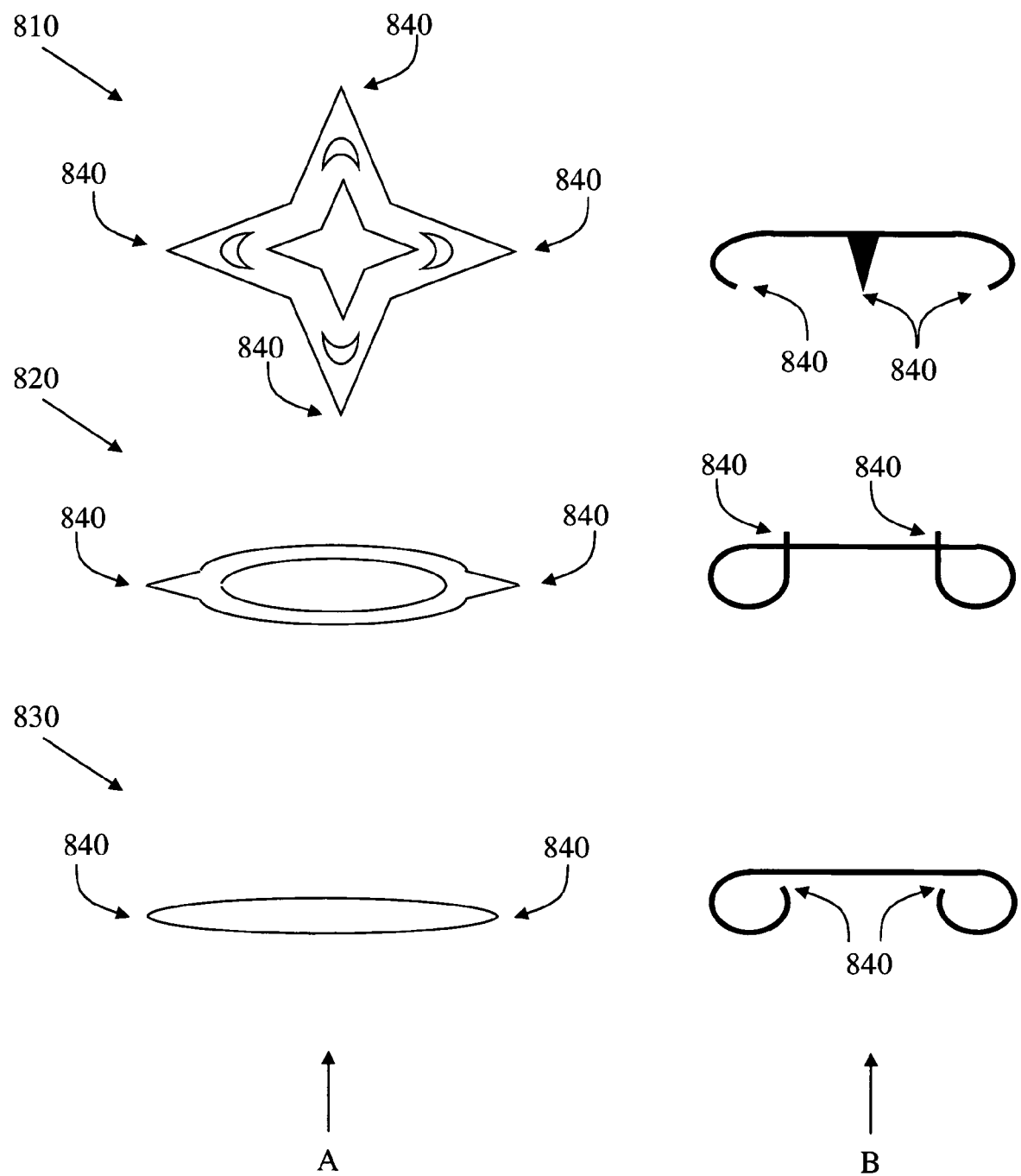
FIG. 8 shows three variations of deployable clips 810, 820, 830 having at least two sharp edges 840. Top views A show clips in an deployed state and side views B show clips in a deployed state with edges 840 in a secured position (note that tissue parts are not shown in B).
Figure 9:
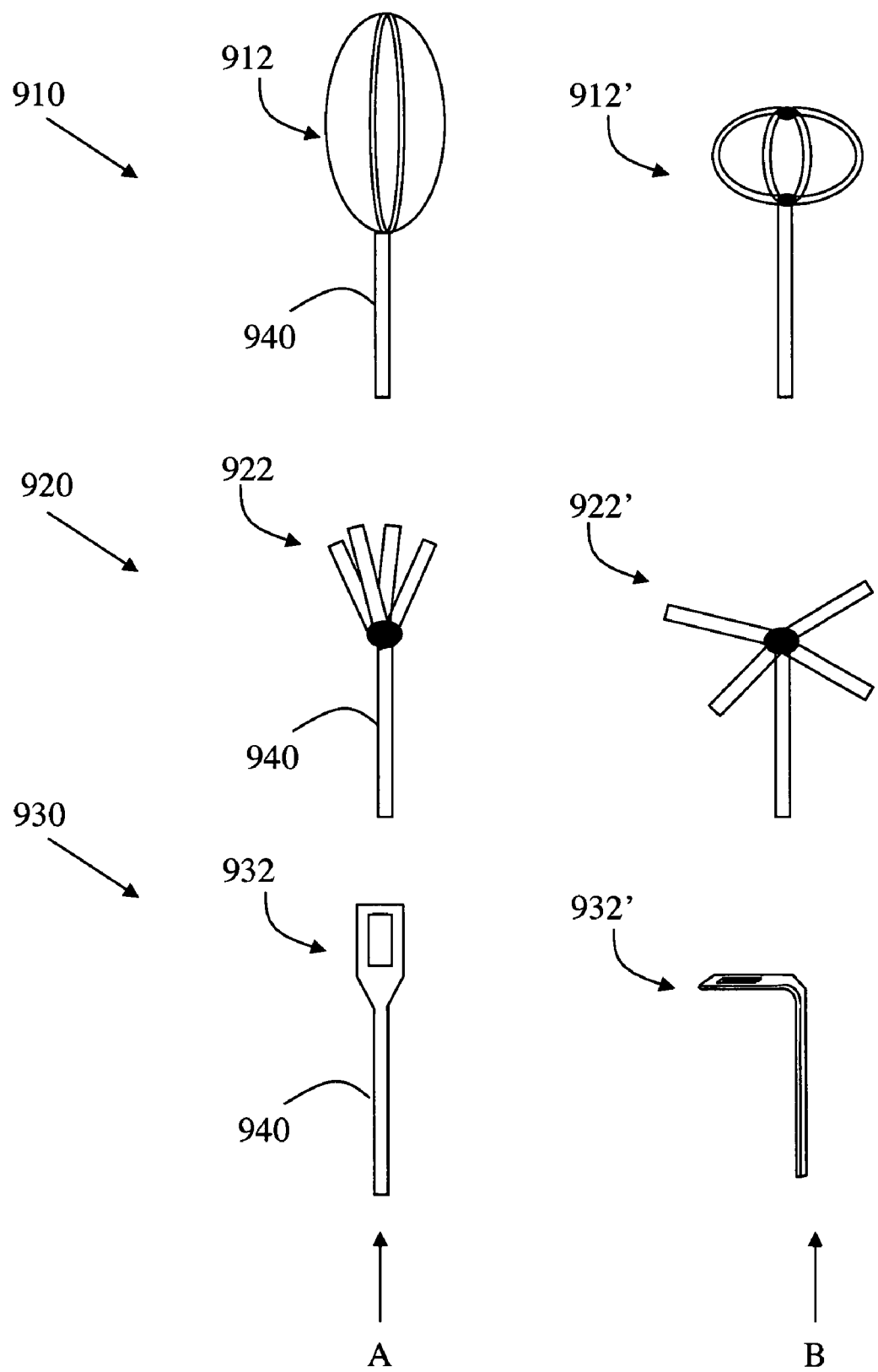
FIG. 9 shows three examples of clip securing mechanisms 910, 920, 930 that will secure deployable clip through the tissue parts. Each clip securing mechanism has a pull-wire (not shown but inside 940) to engage (bent, unfold, uncompress, or expand) the top part 912, 922, 932 from position shown in A to position shown in B (i.e. top part 912', 922', 932').
Figure 10:
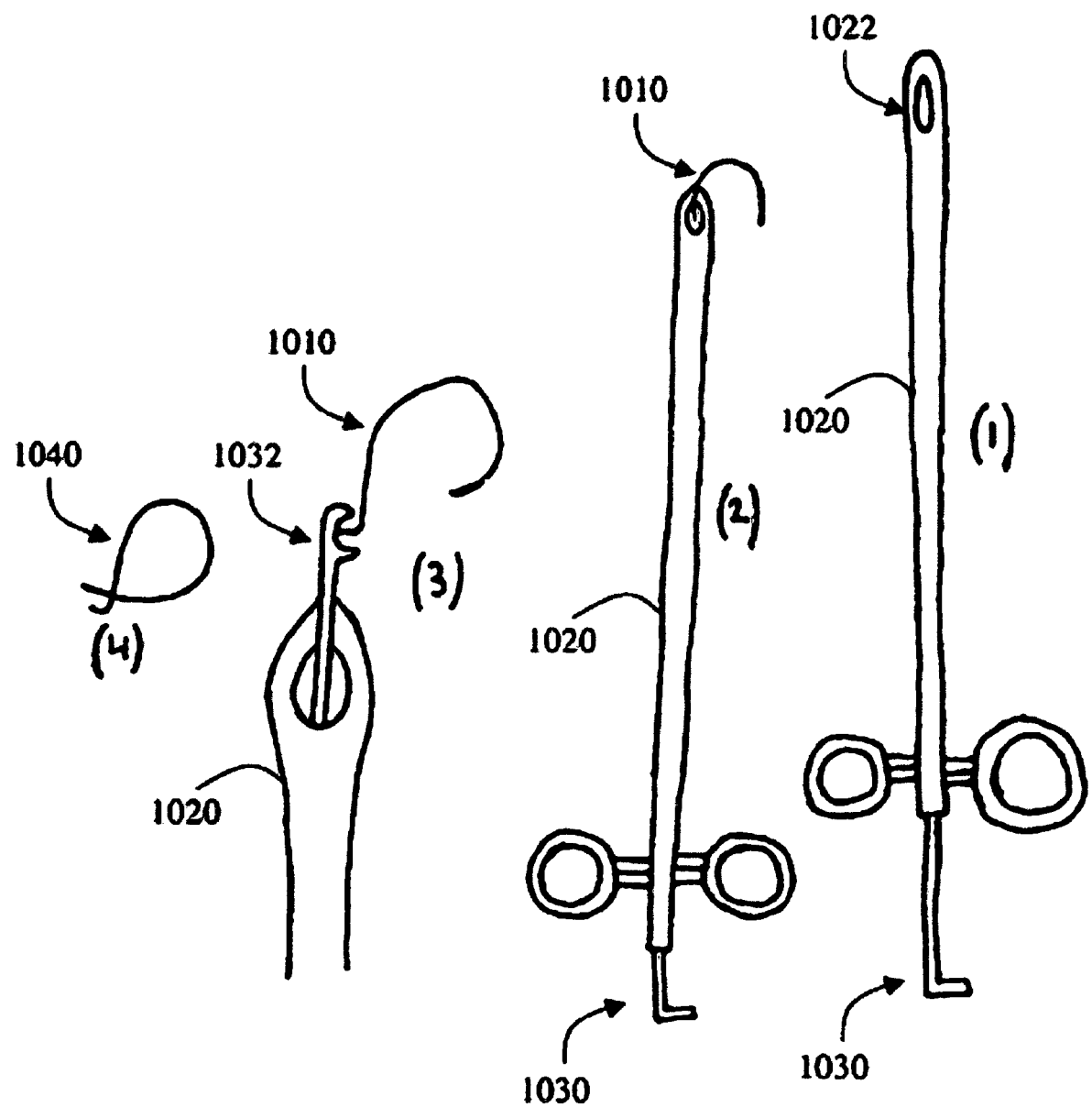
FIG. 10 shows an example of advancing clip 1010 through opening 1022 of second guiding element 1020. An advancing and holding mechanism 1030 for clip 1010 with a clip holding end 1032 is used to advance and manipulate clip 1010. Potentially advancing and holding mechanism 1030 could assist in clipping clip 1010 in position as indicated in 1040.
Figure 11:
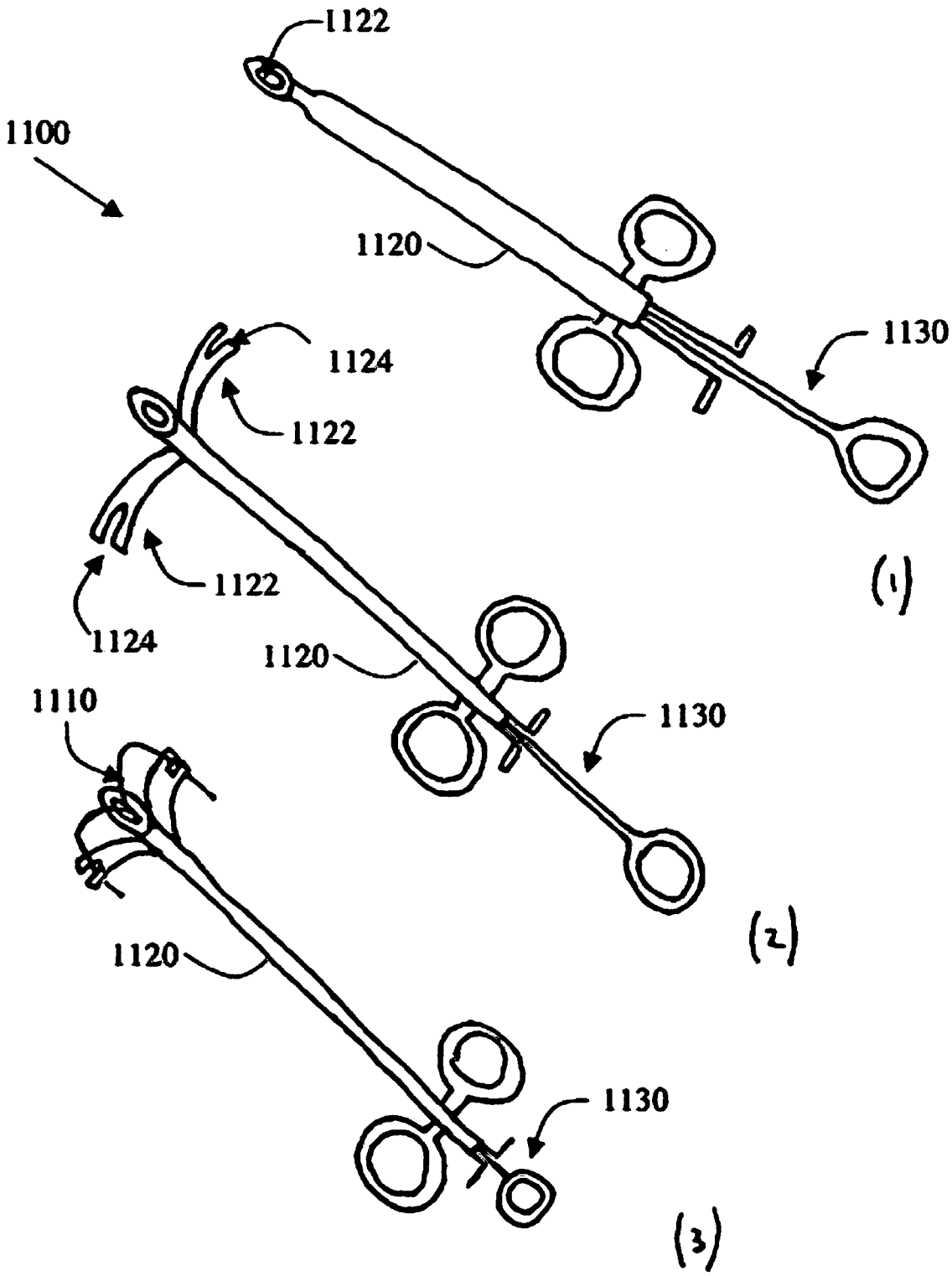
FIG. 11 shows an example of advancing clip 1110 through opening 1122 of second guiding element 1120 (1122 are the wings of second guiding element 1120 with openings 1124). An advancing and holding mechanism 1130 for clip 1110 is used to advance and manipulate clip 1110.
Figure 12:
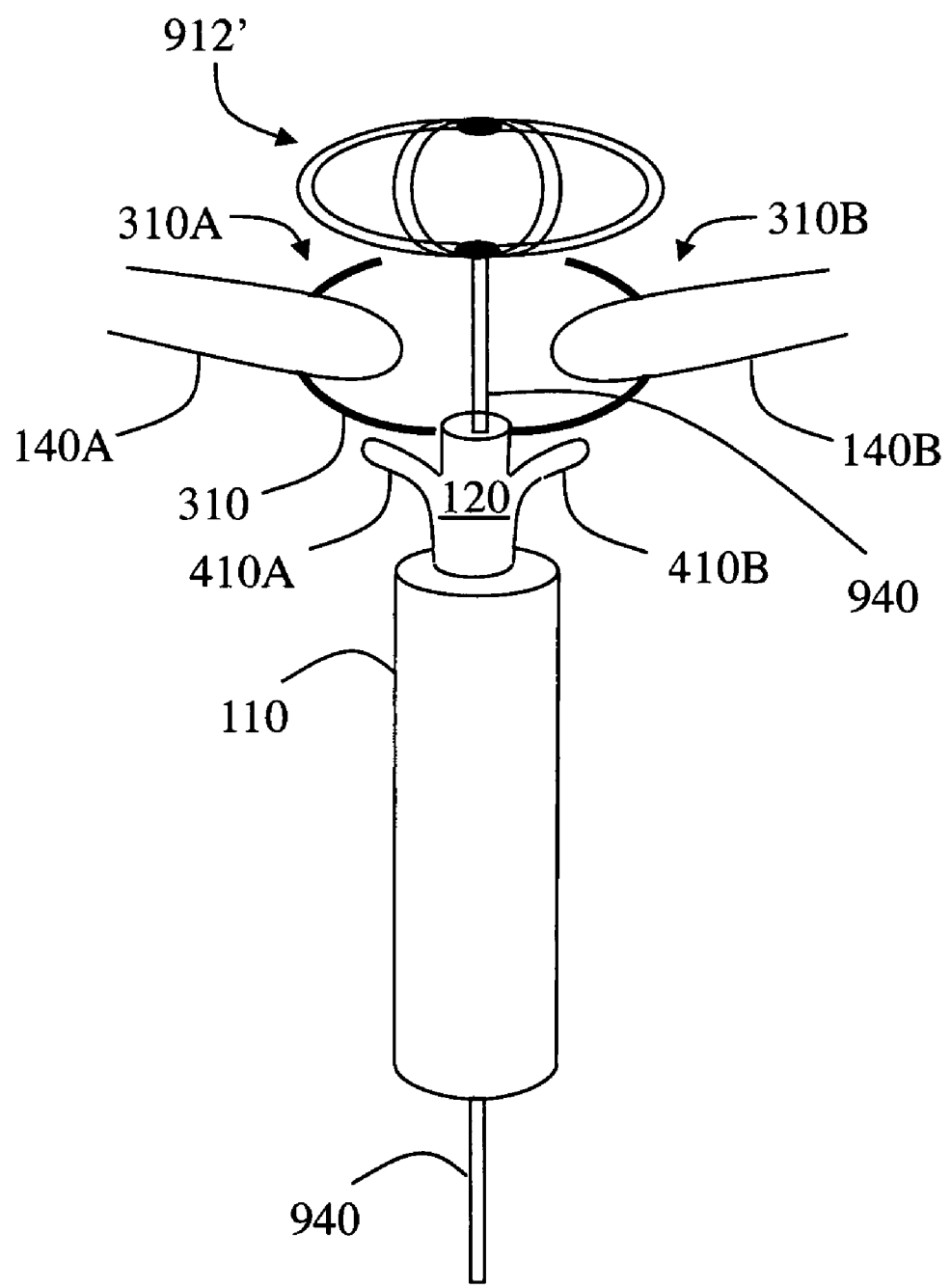
FIG. 12 shows an example of clip securing mechanism 910 where top part 912 (as shown in FIG. 9) is changed to position 912' to assist in securing clip 310.

The present invention provides a useful percutaneous surgical method and device for repairing tissue with minimal invasiveness and maximum effectiveness. In general, a catheter is positioned in a manner as to contact two open edges simultaneously. Depending on applications, the edges could be two flaps, leaflets, walls, muscles, skins, or other types of tissues or organic structures. A stabilizing structure holds the tissue to be joined before the joining is delivered. A clip (also referred to as suture material), or the like, is then delivered to take hold of the two open edges together, e.g., grab the flaps and clip them together. Other joining techniques such as delivery of adhesives, two part adhesives, or surface activated structures through nanotechnology can also be delivered and result in attachment.

Preferably, in a vascular application, for example, a guide wire or guiding catheter is first delivered, either from the left atrium down to the left ventricle or from the left ventricle up to the left atrium. It is also possible to access the left atrium or ventricle through the septum by accessing the right atrium or ventricle via the venous side. A catheter or catheter system is then delivered over the guide wire to reach the desired treatment site. Note that a guide wire can be delivered through a guiding catheter or angiography catheter with proper tip design that is, for example, advanced into the left ventricle via aorta, or at the ostium of the right atrium. It is also possible to introduce these catheters or trocars not through the arterial or venous path but through small incision in the chest and directly into the left ventricle.

In some embodiments, according to an aspect of the invention, the following steps are distinguished:
1. bringing a guiding catheter inside the left ventricle, the guiding catheter may also contain other catheters coaxially;
2. delivering a guide wire through the catheter into the left atrium;
3. delivering and stabilizing the catheter over the guide wire into the left atrium, the stabilizing catheter maybe a system of coaxially positioned catheters;
4. removing the guide wire;
5. removing an outer sheath of the stabilizing catheter to allow two or more previously depressed wings (two or more, either over and/or under the tissue) thereof to open up, each of these wings may have an opening, a window, a through hole, or the like;
6. positioning the stabilizing catheter to allow the wings to contact two open edges or leaflets that needs to be repaired and put together;
7. pushing a folded clip through the center of the catheter until it exits the catheter and opens up after which its ends penetrate the two open leaflets through the openings of the wings; and
8. retrieving the catheter while continuously pushing the clip, thereby causing the clip to separate from the catheter and enter the region of interest, i.e., area to be repaired.

In yet another embodiment of the present invention, a catheter system or trocar is advanced percutaneously into the treatment site and two or more lightweight magnetically charged structures of opposite polarity are delivered across or into the tissue either simultaneously or sequentially. The attraction force between the two magnets will bring the tissues together with minimum effort. In this situation, one can even advantageously eliminate the need for suturing.

As one of ordinary skill in the art will appreciate, the drawings and description disclosed herein illustrate technologies related to the invention, show examples of the invention, and provide examples of using the invention. Various changes, substitutions, modifications, and alterations could be made or otherwise implemented without departing from the principles of the present invention. For example, it is possible to have more than one set of wings. The openings of the wings could have various shapes and dimensions to suit the various sizes and configurations of the clip.

These drawings also show a device and method of stabilizing a surface to be clipped/stapled/sutured or otherwise joined percutaneously, allowing a surgeon to perform more accurately. This includes holding a surface across two opposite walls. If desired, one can slide a third catheter over the stabilizing catheter with wings proximal to the valve leaflets to "sandwich" the leaflet during clipping/stapling. The creation of two layers across the clip/staple allows for extra force on the clip to better position or penetrate the tissues. This additional force can be obtained, for example, by delivering a super-elastic open mesh, basket, retractor, or the like over the suture. Pulling from the proximal end on the deployed structure applies additional force on the clip, thereby facilitating its positioning or penetration in the tissues.

It is also possible to add a flexible pull wire through the entire catheter that is attached to the distal end of the mesh, basket, retractor, or the like. By pulling the wire from the proximal end, and with or without twisting the shaft, one can entirely collapse the basket or the mesh over the clip and apply the additional force thereto.

The catheters (i.e. first and second guiding elements) could be made of nylon, polyethylene or other copolymers, braided or not. It could be reinforced with different structures such as coil metal made of nitinol (a shape memory alloy), stainless steel or Elgiloy® (a cobalt-chromium-nickel alloy). The inner shaft of the catheter may contain Teflon® (a non-stick protective coating) or other lubricious materials. Coatings maybe added on outer surface of catheters to allow easy movement. The material of braiding or coil can be nitinol, stainless steel, Elgiloy®, or similar flexible materials. Radiopaque markers rings or band such as platinum, gold, or alloys can be embedded or positioned at different locations of the catheter, for example, at the distal end to allow visibility under x-ray. Markers can be positioned at the proximal end as a landmark to control catheter advancement.

The stabilizing wings could be made of flexible materials such as polymers or metallic alloys. These include polypropylene, nitinol, stainless steel, shape memory materials, including metallic shape memory materials, whether super-elastic or heat recoverable.

The clip could be in the form of a simple needle that is sharpened at both ends and is flexible. Alternatively, it may have more of a three dimensional shape such as an open disc with sharp edges curved inward or outward for better penetration. The clip may be folded and delivered through the main delivery system alone or between two supporting members to avoid uncontrolled popping outside the catheter.

In some embodiments the clip has two or more sharp edges, e.g. 4. These edges could be at each corner of a square, or take any position of any shape clip.

The clip can be made of numerous materials metallic, magnetic or non-metallic known to those skilled in the art. For example, super-elastic nitinol in the binary nickel-titanium (Ni—Ti) or Ni—Ti with a third or fourth element added such as V, Mo, Fe, Cr, W, Nb. Other super-elastic alloys include iron based shape memory alloys. The clip maybe made from shape memory polymers such poly-ethylenes. It is also possible to make the clip/staple from a composite material, i.e., a combination of plastics or metallic alloys. It is further possible to make the staple from a combination of monomers and polymers and, after delivery, activate the monomeric section to polymerize, thereby causing diffusion within the structure. This diffusion will create tension or compression in the staple and cause tightening or loosening in the desired section and allow better joining of the tissues. Many activation techniques such as light are available to deliver percutaneously to cause or affect shape changes. The clips could also be of dis-similar or similar magnets across the tissue to hold the tissue open or closed.

In addition, the clip could be coated with lubricious coatings, antithrombogenic coatings such as heparin or active peptide coatings, e.g., P15. It is also possible to cover the metallic staple with other polymers like silicone or polyurethane. These surface modifications may also be obtained through etching, plasma etching or at the molecular level such as nanostructures, nanowires or nanotubes via nanotechnology methods.

Heat recoverable shape memory materials, polymeric or metallic could also be used for the clip or suturing material. In this case, the clip/staple is delivered and it changes shape either by naturally warming up with body temperature or heated via electrical heating or convection heating. The electrical heating maybe achieved through wiring across the catheter using a good conductor, such as gold or gold plated metallic wire. It is also possible to use temporary wide hysteresis shape memory materials such as Ni—Ti—Nb or Ni—Ti—Mo for the clip/staple. In this case, the material is heated to its super-elastic shape without the risk of transitioning to a sifter temperature upon cooling.

Stabilizers could also be balloons made of PE, Cfelx™ or silicone. These designs better control the final shape by the amount of balloon inflation. It is known to those skilled in the art that similar approach can be made through trocars instead of a guiding catheter when performing laparoscopic surgery to treat obesity, for example.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For instance, the stabilizing and clip suturing technique, devices, and materials disclosed herein are not limited to cardiovascular applications and can be utilized in or otherwise implemented for various applications and treatments, for instances, obesity. All such variations are considered to be within the scope and spirit of the present invention as defined by the following claims and their legal equivalents.

What is claimed is:

1. A device for repairing tissue, comprising:
   (a) a first guiding element with a first opening;
   (b) a second guiding element with a second opening movable through said first opening of said first guiding element;
   (c) a first set of at least self-deployable wings provided on said second guiding element, said first set of wings having an un-deployed state in which said wings are maintained in folded or compressed position to facilitate passage through said first guiding element, and a self-deployed state in which said wings self-deploy as they are advanced past said first opening of said first guiding element, said wings being configured to engage two or more tissue parts in said self-deployed state and stabilize said second guiding element with respect to said tissue parts;
   (d) a self-deployable clip having two or more edges capable of penetrating said two or more tissue parts, said self-deployable clip having an un-deployed state for advancing through said first or said second opening and a self-deployed state for when advanced past said first or said second opening respectively;
   (e) means for guiding said self-deployable clip into said tissue parts; and
   (f) a clip securing mechanism movable through said second opening, said clip securing mechanism having a top part with a first state for advancing through said second guiding element and a second state whereby said top part is bend, unfolded or uncompressed and capable of securing said self-deployable clip through said tissue parts.

2. The device as set forth in claim 1, wherein said two or more tissue parts are flaps of a left atrium.

3. The device as set forth in claim 1, wherein said deployable clip has at least one of a lubricous coating or a radiopaque marker.

4. The device as set forth in claim 1, wherein said clip securing mechanism comprises a pull-wire.

5. The device as set forth in claim 1, wherein said self-deployable clip comprises magnetic material, shape memory alloy or nitinol.

6. The device as set forth in claim 1, wherein said second guiding element further comprises another set of self-deployable wings on the outside of said second guiding element, wherein said other set of wings having a un-deployed state to move through said first guiding element, and a deployed state for when advanced passed said first opening of said first guiding element, and wherein said other set of wings in said self-deployed state are capable of stabilizing two or more tissue parts with respect to said device together with said two or more self-deployable wings.

7. The device as set forth in claim 1, wherein said means for guiding is a second opening defined in two or more wings of said first set of wings.

* * * * *